(12) United States Patent
Zhang et al.

(10) Patent No.: US 11,812,770 B2
(45) Date of Patent: Nov. 14, 2023

(54) LACTOBACILLUS PARACASEI 207-27 AND USE THEREOF

(71) Applicant: BYHEALTH CO., LTD., Guangdong (CN)

(72) Inventors: Xuguang Zhang, Guangdong (CN); Xiaolei Ze, Guangdong (CN); Ruikun He, Guangdong (CN); Fang He, Guangdong (CN)

(73) Assignee: BYHEALTH CO., LTD., Guangdong (CN)

( * ) Notice: Subject to any disclaimer, the term of this patent is extended or adjusted under 35 U.S.C. 154(b) by 0 days.

(21) Appl. No.: 17/638,082

(22) PCT Filed: Feb. 1, 2021

(86) PCT No.: PCT/CN2021/074672
§ 371 (c)(1),
(2) Date: Feb. 24, 2022

(87) PCT Pub. No.: WO2022/041656
PCT Pub. Date: Mar. 3, 2022

(65) Prior Publication Data
US 2023/0085303 A1 Mar. 16, 2023

(30) Foreign Application Priority Data

Aug. 24, 2020 (CN) .......................... 202010858415.8

(51) Int. Cl.
*A23L 2/39* (2006.01)
*A23L 33/135* (2016.01)
(Continued)

(52) U.S. Cl.
CPC ................ *A23L 2/39* (2013.01); *A23C 9/127* (2013.01); *A23C 9/1234* (2013.01); *A23G 3/366* (2013.01);
(Continued)

(58) Field of Classification Search
None
See application file for complete search history.

(56) References Cited

U.S. PATENT DOCUMENTS

| | | | |
|---|---|---|---|
| 2005/0214271 A1* | 9/2005 | Hsu | ........................ C12N 1/20 435/252.9 |
| 2011/0150838 A1* | 6/2011 | Chang | ..................... A61P 43/00 435/252.9 |

(Continued)

FOREIGN PATENT DOCUMENTS

| | | |
|---|---|---|
| CN | 104894021 A | 9/2015 |
| CN | 105368738 A | 3/2016 |

(Continued)

OTHER PUBLICATIONS

English translation of the International Search Report and Written Opinion in PCT/CN2021/074672, dated Jun. 1, 2021.

(Continued)

*Primary Examiner* — Felicia C Turner
(74) *Attorney, Agent, or Firm* — MEDLER FERRO WOODHOUSE & MILLS PLLC

(57) ABSTRACT

The present application relates to a *Lactobacillus paracasei* or progeny thereof. Specifically, the present application relates to *Lactobacillus paracasei* 207-27 and a composition, culture, food product or dietary supplement containing the same. The present application also relates to the use of *Lactobacillus paracasei* 207-27 and the composition, culture, food product or dietary supplement containing the same in medicine.

11 Claims, 1 Drawing Sheet

(51) Int. Cl.
  *C12N 1/20*   (2006.01)
  *A23C 9/123*  (2006.01)
  *A23C 9/127*  (2006.01)
  *A23G 3/36*   (2006.01)
  *A23L 2/38*   (2021.01)
  *C12R 1/225*  (2006.01)

(52) U.S. Cl.
  CPC ............ *A23L 2/382* (2013.01); *A23L 33/135* (2016.08); *C12N 1/205* (2021.05); *C12R 2001/225* (2021.05)

(56) References Cited

U.S. PATENT DOCUMENTS

| | | | |
|---|---|---|---|
| 2012/0122189 A1 | 5/2012 | Hsiao et al. | |
| 2018/0256654 A1* | 9/2018 | Chen | A61P 19/10 |
| 2021/0077550 A1 | 3/2021 | Ko et al. | |

FOREIGN PATENT DOCUMENTS

| | | |
|---|---|---|
| CN | 107916236 A | 4/2018 |
| CN | 108373984 A | 8/2018 |
| CN | 111117907 A | 5/2020 |
| CN | 111286474 A | 6/2020 |
| CN | 111944725 A | 11/2020 |
| EP | 2581461 A1 | 4/2013 |
| WO | 9929833 A1 | 6/1999 |
| WO | 2011076007 A1 | 6/2011 |

OTHER PUBLICATIONS

Dong et al., "Immunomodulatory effects of lactic acid bacteria on gut-associated immune system: research progress," Chinese Journal of Microecology 26(2):221-242 (2014). (English abstract only.).

Mantzourania et al., "Effect of a novel Lactobacillus paracasei starter on sourdough bread quality," Food Chemistry 271:259-265 (2019).

Yang et al., "Regulating Effect of Lactobacillus paracasei L9 on Th1/Th2 Balancing in Allergic Mouse's Splenocytes," Journal of Chinese Institute of Food Science and Technology 17(4):14-20 (2017). (English abstract only.).

Zhang et al., "Review on the Probiotic Characteristics and Application of Lactobacillus Paracasei," Packaging and Food Machinery 37(4):47-52 (2019). (English abstract only.).

IPA International Probiotics Association, IPA guidelines to qualify a microorganism to be termed as 'probiotic', 2017. https://internationalprobiotics.org/wp-content/uploads/20170602-IPA-guidelines-to-qualify-a-microorganism-as-probiotic.pdf.

FAO/WHO, Joint FAO/WHO Working Group Report on Drafting Guidelines for the Evaluation of Probiotics in Food, 2002. http://www.who.int/foodsafety/publications/fs_management/probiotics2/en/.

HOWARU strains LPC-37, retrieved Jul. 12, 2023: https://www.howaru.com/hcp/strains/lpc-37/.

* cited by examiner

LACTOBACILLUS PARACASEI 207-27 AND USE THEREOF

TECHNICAL FIELD

The present application relates to *Lactobacillus paracasei* or progeny thereof. Specifically, the present application relates to a *Lactobacillus paracasei* 207-27 and a composition, culture, food product or dietary supplement comprising the same. The present application also relates to a use of *Lactobacillus paracasei* 207-27 and composition, culture, food product or dietary supplement comprising the same in the manufacture of a medicament or health care product.

BACKGROUND

70%-80% of the human body's immune cells are located in the human intestine. At the same time, the total number of bacteria in the human intestine can reach 100 trillions, accounting for about 78% of the total human microbes. Therefore, the intestine provides an important platform for the host immune system to interact with microorganisms. The Food and Agriculture Organization of the United Nations (FAO) and the World Health Organization (WHO) believe that probiotics are living microorganisms that, when administered in adequate amounts, confer a health benefit on the host. A large number of in vitro tests and clinical trials have shown that probiotics have good application effects in host intestinal health and immune regulation.

Probiotics can regulate host immune function through a variety of mechanisms. In terms of mucosal barrier function, probiotics can compete with invading organisms for attachment sites on mucosal cells, thereby preventing bacteria from penetrating mucosa and entering deep tissues; regulating the tight junctions among intestinal epithelial cells and strengthening the barrier function of mucosal cells; inhibiting the dissolution and apoptosis of intestinal mucosal cells and maintaining the integrity of gastrointestinal mucosa. Probiotics can also enhance innate immune function by enhancing the phagocytic activity of antigen-presenting cells (APCs) such as phagocytes, DCs, enhancing the killing ability of NK cells, and enhancing the expression level of cytokines (e.g., pro-inflammatory factors such as IL-12, IFN-γ, TNF-α and anti-inflammatory factors such as TGF-β, IL-10, etc.) to control the intensity of the inflammatory response. At the same time, probiotics can enhance adaptive immunity. The probiotics colonized at the intestinal mucosa can promote the responsiveness of T and B lymphocytes to antigen stimulation, stimulate the relevant lymphoid tissues in the intestinal mucosa, and induce the secretion of sIgA. Probiotics as antigenic substances can be phagocytosed by M cells. The antigen in M cells is quickly released and taken up by DCs, which presents the antigen to naive CD4+ T lymphocytes, activating Th1 or Th2 cells to balance the ratio of Th1 and Th2 reactions.

In addition, whether probiotics such as lactic acid bacteria can exert the above health benefit on the body also depends on whether the strain can tolerate the defense mechanism of the gastrointestinal tract in the body, such as the low pH environment in gastric juice and the bile acid in small intestine. Only when they reach the intestine alive, adhere to the intestinal epithelial cells and colonize in the intestine, they can produce beneficial metabolites and interact with the host.

Therefore, screening for lactic acid bacteria that can enter the intestines and have high viability is the primary consideration for the development of probiotics. Probiotics with high survivability, as well as the ability to regulate the host's immune function and anti-allergic function are yet to be developed.

Contents of the Invention

In the present invention, unless otherwise specified, the scientific and technical terms used herein have the meanings commonly understood by those skilled in the art. At the same time, in order to better understand the present invention, definitions and explanations of related terms are provided below.

As used herein, the term "progeny" refers to progeny cells produced by microorganisms through growth (e.g., growth by culturing in culture medium). It is easy to understand that in the growth and culture of microorganisms, especially bacteria, certain changes (e.g., mutation of one or several bases) may occur in genetic material, and these changes may occur spontaneously or may be the results of mutagenesis with chemical and/or physical agents (e.g., mutagens) and/or recombinant DNA technology known in the art. Therefore, the progeny of *Lactobacillus paracasei* herein is intended to encompass the progeny whose genetic material has not changed or has changed as compared with the *Lactobacillus paracasei* of the present invention. Of course, the progeny still retain the functions of the strain from which they are derived (e.g., capable of enhancing immunity, improving allergic reactions, etc.).

As used herein, the term "pharmaceutically acceptable carrier" refers to a carrier that is pharmacologically and/or physiologically compatible with the subject and the active ingredient, which is well known in the art (see, for example, Remington's Pharmaceutical Sciences. Edited by Gennaro A R, $19^{th}$ ed. Pennsylvania: Mack Publishing Company, 1995), and includes but not limited to: pH adjusting agents, surfactants, adjuvants, ionic strength enhancers. For example, pH adjusting agents include, but are not limited to, phosphate buffer; surfactants include, but are not limited to, cationic, anionic or nonionic surfactants, such as Tween-80; and ionic strength enhancers include, but are not limited to, sodium chloride.

As used herein, the term "dietary supplement" refers to an edible product that can provide consumers with beneficial effects (e.g., nutritional effects, preventive effects, therapeutic effects, or other beneficial effects). In this context, the dietary supplement covers health care products, nutritional products, supplements and other products.

As used herein, the term "medicament" encompasses medicament used in both human and animal in human medicine and veterinary medicine, as well as those used for incorporation into animal feed (e.g., livestock feed and/or pet food). In addition, the term "medicament" as used herein means any substance that provides therapeutic, preventive, and/or beneficial effects. The term "medicament" as used herein is not necessarily limited to substances that require a marketing approval, but includes materials that can be used in cosmetics, health care products, food (including, for example, feed and beverages), probiotic cultures, and dietary supplements.

As used herein, the term "CFU (Colony-Forming Units)" refers to the total number of microbial colony such as bacteria, fungi and yeast in a product, and is usually used for the calculation of viable count.

As used herein, the term "CFU/dose" refers to the amount of bacteria present in the composition/food product or dietary supplement/pharmaceutical composition provided to the subject every day or every time. For example, in certain embodiments, *Lactobacillus paracasei* in the food product or dietary supplement is present in an amount of $10^6$ to $10^{12}$ CFU/dose (e.g., $10^8$ to $10^{12}$ CFU/dose). In this embodiment, if *Lactobacillus paracasei* is applied in a food product (e.g., in solid beverages, yogurt), the food product (e.g., solid beverages, yogurt) provided to the subject every day or every time may contain about $10^6$ to $10^{12}$ CFU of *Lactobacillus paracasei*. Of course, alternatively, the amount of such bacteria can be divided into and administered in a plurality of batches. As long as the total amount of *Lactobacillus paracasei* received by the subject at any specific time (e.g., a period of every 24 hours) is from about $10^6$ to about $10^{12}$ CFU, it meets the requirement of the above-mentioned food product or dietary supplement in which *Lactobacillus paracasei* is present in an amount of $10^6$ to $10^{12}$ CFU/dose (e.g., $10^8$ to $10^{12}$ CFU/dose).

The inventors of the present application selected a strain of *Lactobacillus paracasei* with significant strain-specific probiotic potential from 265 strains derived from the intestinal tract of healthy newborns through a large number of experiments. The inventors of the present application have confirmed through a large number of experiments that the *Lactobacillus paracasei* has good tolerance to the acidic environment of gastric juice and bile salts, has high capability to adhesion to the intestinal tract, and can enhance immunity, improve or alleviate allergies symptoms, and thus completed the present invention.

Therefore, in a first aspect, the present application provides a *Lactobacillus paracasei* or progeny thereof, the *Lactobacillus paracasei* is deposited in the Guangdong Microbial Culture Collection Center, and has an accession number of GDMCC No. 60960.

In a second aspect, the present application provides a composition comprising the *Lactobacillus paracasei* or progeny thereof.

In certain embodiments, the composition further comprises a microorganism selected from the group consisting of bacterium, fungus (e.g., yeast), or any combination thereof.

In certain embodiments, the *Lactobacillus paracasei* may be used in combination with one or more other species of microorganisms, in which the other species of microorganisms can have a beneficial effect on the health of a host to which it is administered.

In certain embodiments, the microorganism is a probiotic.

In certain embodiments, the probiotic is selected from probiotic bacterium, yeast, or any combination thereof.

As used herein, the term "probiotic bacterium" is defined as any non-pathogenic bacterium, and when it as live bacterium is administered in a sufficient amount to a host, it can have a beneficial effect on the health of the host.

In certain embodiments, the bacterium is selected from the group consisting of *Lactobacillus* spp., *Bifidobacterium* spp., *Bacillus* spp., *Propionibacterium* spp., *Streptococcus* spp., *Lactococcus* spp., *Pediococcus* spp., *Enterococcus* spp., *Staphylococcus* spp., or any combination thereof.

In some embodiments, the bacterium of the *Lactobacillus* spp. is selected from the group consisting of: *Lactobacillus paracasei, Lactobacillus acidophilus, Lactobacillus brevis, Lactobacillus jensenii, Lactobacillus iners, Lactobacillus casei, Lactobacillus crispatus, Lactobacillus curvatus, Lactobacillus delbrueckii, Lactobacillus fermentum, Lactobacillus gasseri, Lactobacillus helveticus, Lactobacillus johnsonii, Lactobacillus plantarum, Lactobacillus reuteri, Lactobacillus rhamnosus, Lactobacillus sakei, Lactobacillus salivarius*, or any combination thereof.

In certain embodiments, the bacterium of the *Bifidobacterium* spp. is selected from the group consisting of: *Bifidobacterium animalis, Bifidobacterium bifidum, Bifidobacterium breve, Bifidobacterium infantis, Bifidobacterium longum, Bifidobacterium adolescentis*, or any combination thereof.

In certain embodiments, the bacterium of the *Bacillus* spp. is selected from the group consisting of: *Bacillus subtilis, Bacillus coagulans*, or any combination thereof.

In certain embodiments, the bacterium of the *Propionibacterium* spp. is selected from the group consisting of: *Propionibacterium shermanii, Propionibacterium freudenreichii, Propionibacterium acidipropionici*, or any combination thereof.

In certain embodiments, the bacterium of the *Streptococcus* spp. is selected from the group consisting of: *Streptococcus thermophilus, Streptococcus salivarius*, or any combination thereof.

In certain embodiments, the bacterium of the *Lactococcus* spp. is *Lactococcus lactis*. In certain embodiments, the bacterium of the *Enterococcus* spp. is selected from the group consisting of: *Enterococcus faecalis, Enterococcus faecium*, or any combination thereof.

In certain embodiments, the yeast is selected from the group consisting of *Saccharomyces cerevisiae, Saccharomyces boulardii, Kluyveromyces marxianus*, or any combination thereof.

In certain embodiments, the composition further comprises an additional additive.

Those skilled in the art can select and adjust the additional additive according to requirements. In certain embodiments, the additional additive is selected from the group consisting of other nutrient, mineral, vitamin, or any combination thereof.

In certain embodiments, the additional additive can have a beneficial effect on the health of the host to which it is administered.

In certain embodiments, the other nutrient is selected from the group consisting of dietary fiber, prebiotics, protein (e.g., enzymes), carbohydrate, lipid (e.g., fat), mineral, vitamin, plant ingredient (e.g., plant extract), amino acid, immunomodulator, milk substitute, or any combination thereof.

In certain embodiments, the mineral is selected from the group consisting of iron, zinc, potassium, sodium, calcium, magnesium, and any combination thereof.

In certain embodiments, the vitamin is selected from the group consisting of vitamin B1, vitamin B2, vitamin B6, vitamin B12, vitamin A, vitamin C, vitamin D, vitamin E, vitamin K, and any combination thereof.

In some embodiments, the composition serves as a starter culture (e.g., starter culture for plant fermented product, starter culture for dairy product). In such embodiments, the *Lactobacillus paracasei* in the composition is used as a starter culture to participate in a fermentation process. For example, in the process of preparing yogurt, *Lactobacillus paracasei*, as a probiotic, is fermented together with fresh milk to prepare yogurt.

In certain embodiments, the composition is used to prepare a food product and/or a dietary supplement (e.g., health care food).

In certain embodiments, the food product is selected from the group consisting of solid beverage, candy, or fruit juice; or, the food product is a dairy product (e.g., yogurt, flavored fermented milk, lactic acid bacteria beverage, cheese).

In certain embodiments, the dietary supplement is formulated for oral administration.

In certain embodiments, the dietary supplement is in the form of a pill, powder, capsule, tablet, granule powder, opercula, orally dissolving granule, sachet, dragee or liquid.

In some embodiments, preferably, *Lactobacillus paracasei* is present in the composition in an amount of $10^6$ to $10^{12}$ CFU/dose (e.g., $10^8$ to $10^{12}$ CFU/dose).

In a third aspect, the present application provides a food product or dietary supplement comprising the aforementioned *Lactobacillus paracasei* or progeny thereof or the aforementioned composition.

In the context, the term "food" is broad, including human food and drinks, as well as animal food and drinks (i.e., feed). In certain embodiments, the food product is suitable and designed for human consumption.

It can be understood that, depending on the use, application mode or administration mode, the food product of the present application may be in the form of liquid, solid, suspension or powder.

In certain embodiments, the food product is selected from the group consisting of solid beverage, candy or fruit juice, or the food product is a dairy product (e.g., yogurt, flavored fermented milk, lactic acid bacteria beverage, cheese).

In certain embodiments, the dietary supplement is formulated for oral administration.

In certain embodiments, the dietary supplement is in the form of a pill, powder, capsule, tablet, granule powder, opercula, orally dissolving granule, sachet, dragee or liquid.

In certain embodiments, the food product or dietary supplement may also comprise (but not limited to) one or any combination of the following substances: probiotic (e.g., probiotic bacterium), dietary fiber, prebiotics, protein (e.g., enzyme), carbohydrate, lipid (e.g., fat), vitamin, mineral, plant ingredient (e.g., plant extract), amino acid, immunomodulator, milk substitute, or metabolite or extract of *Bifidobacterium breve* or progeny thereof. In some embodiments, the composition of the present invention can also be combined with different sweeteners or flavoring agents, toning substances, stabilizers, glidants, fillers and other auxiliary materials that are acceptable in foods.

In certain embodiments, *Lactobacillus paracasei* or progeny thereof is present in the form of a concentrate.

In certain embodiments, the *Lactobacillus paracasei* in the food product or dietary supplement is present in an amount of $10^6$ to $10^{12}$ CFU/dose (e.g., $10^8$ to $10^{12}$ CFU/dose).

In a fourth aspect, the present application provides a pharmaceutical composition comprising the aforementioned *Lactobacillus paracasei* or progeny thereof.

As used herein, the term "pharmaceutical composition" encompasses pharmaceutical compositions used in humans as well as pharmaceutical compositions used in animals (e.g., veterinary applications). In certain embodiments, the pharmaceutical composition is for use in humans.

In certain embodiments, the pharmaceutical composition comprises a formulation of *Lactobacillus paracasei*.

In certain embodiments, the pharmaceutical composition comprises a pharmaceutically acceptable carrier.

In certain embodiments, the pharmaceutical composition is formulated for oral administration.

In some embodiments, the pharmaceutical composition is in the form of a pill, powder, capsule, tablet, granule powder, opercula, orally dissolving granule, sachet, dragee or liquid.

Preferably, *Lactobacillus paracasei* in the pharmaceutical composition is present in an amount of $10^6$ to $10^{12}$ CFU/dose (e.g., $10^8$ to $10^{12}$ CFU/dose).

In a fifth aspect, the present application provides a culture, which comprises the aforementioned *Lactobacillus paracasei* or progeny thereof.

In certain embodiments, the culture further comprises a microorganism selected from the group consisting of bacterium, fungus (e.g. yeast), or any combination thereof.

In certain embodiments, the culture further comprises a nutrient-providing ingredient (e.g., solid or liquid medium, feeder cell layer).

In some embodiments, the nutrient-providing ingredient is selected from the group consisting of prebiotics, protein (e.g., enzyme), carbohydrate, lipid (e.g., fat), probiotic, vitamin, immunomodulator, milk substitute, mineral, amino acid, or any combination thereof.

In certain embodiments, the culture further comprises a cell-free culture filtrate of *Lactobacillus paracasei* or progeny thereof.

In certain embodiments, the culture further comprises a derivative of *Lactobacillus paracasei* or progeny thereof.

In certain embodiments, the derivative is selected from the group consisting of metabolite, enzyme, cellular structural component (e.g., cell wall or component thereof), extracellular polysaccharide, bacteriocin, compound containing immunogenic component, or any combination thereof.

In certain embodiments, the microorganism may be in any form, for example, alive or dead, as a lysate or extract, or as a bacterial product, or as a supernatant.

In a sixth aspect, the present application provides a use of the aforementioned *Lactobacillus paracasei* or progeny thereof or the aforementioned composition or the aforementioned pharmaceutical composition or the aforementioned culture in the manufacture of a medicament or dietary supplement or health care product, the medicament or dietary supplement or health care product is used for inhibiting inflammation or alleviating an inflammatory disease in a subject, or for improving the immunity of the subject, or for preventing a bacterial or viral infection or an autoimmune disease in the subject, or for improving or alleviating an allergic reaction or related symptom in the subject.

In certain embodiments, the inflammatory disease is selected from the group consisting of a disease caused by retina inflammation (e.g., retinitis, keratitis), a disease caused by skin inflammation (e.g., dermatitis, eczema), a disease caused by respiratory tract inflammation (e.g., upper respiratory tract infection), and a disease caused by digestive tract inflammation (e.g., inflammatory bowel disease).

In certain embodiments, the bacterial or viral infection is selected from the group consisting of bacterial influenza, viral influenza, urinary tract infection, vaginitis and cervicitis.

In certain embodiments, the autoimmune disease is selected from the group consisting of systemic lupus erythematosus, diabetes, rheumatoid arthritis, and autoimmune encephalitis.

In certain embodiments, the allergic reaction or related symptom is selected from the group consisting of eczema, atopic dermatitis, asthma, and food allergy.

In some embodiments, the medicament or dietary supplement or health care product can promote the activation of immune cells, promote the production of cytokines, inhibit inflammation or alleviate inflammatory diseases.

In certain embodiments, the cytokine is selected from the group consisting of IL-10, IL-6, IL-12, TNF-α, or any combination thereof.

In certain embodiments, the anti-inflammatory cytokine is IL-10.

In some embodiments, the medicament or dietary supplement or health care product can reduce IgE level and inhibit IgE-mediated allergic reaction.

In some embodiments, the medicament or dietary supplement or health care product is used alone or in combination with an additional antifungal agent, analgesic, anti-inflammatory drug, healing agent, or moisturizer.

In certain embodiments, the subject is a mammal.

In certain embodiments, the subject is a human.

In a seventh aspect, the present invention provides a method for inhibiting an inflammation or alleviating an inflammatory disease, or preventing a bacterial or viral infection or an autoimmune disease, or improving or alleviating an allergic reaction or a symptom thereof, wherein the method comprises: administering the aforementioned *Lactobacillus paracasei* or progeny thereof or the aforementioned composition or the aforementioned pharmaceutical composition to a subject in need thereof.

In certain embodiments, the inflammatory disease is selected from the group consisting of a disease caused by retina inflammation (e.g., retinitis, keratitis), a diseases caused by skin inflammation (e.g., dermatitis, eczema), a disease caused by respiratory tract inflammation (e.g., upper respiratory tract infection), and a disease caused by digestive tract inflammation (e.g., inflammatory bowel disease).

In certain embodiments, the bacterial or viral infection is selected from the group consisting of bacterial influenza, viral influenza, urinary tract infection, vaginitis and cervicitis.

In certain embodiments, the autoimmune disease is selected from the group consisting of systemic lupus erythematosus, diabetes, rheumatoid arthritis, autoimmune encephalitis, and the like.

In certain embodiments, the allergic reaction or related symptom thereof is selected from the group consisting of eczema, atopic dermatitis, asthma, and food allergy.

In certain embodiments, the aforementioned *Lactobacillus paracasei* or progeny thereof or the aforementioned pharmaceutical composition is administered by a method selected from the group consisting of oral administration, injection administration (e.g., intravenous injection or intramuscular injection), topical application (e.g., smearing), or any combination thereof.

In certain embodiments, the aforementioned *Lactobacillus paracasei* or progeny thereof or the aforementioned pharmaceutical composition is administered alone, or in combination with other antifungal agent, analgesic, anti-inflammatory drug, healing agent, or moisturizer.

In certain embodiments, the subject is a mammal.

In certain embodiments, the subject is a human.

In an eighth aspect, the present invention provides a method for improving an immunity of a subject, the method comprising: administering the aforementioned *Lactobacillus paracasei* or progeny thereof or the aforementioned composition or the aforementioned pharmaceutical composition to a subject in need thereof.

In certain embodiments, the aforementioned *Lactobacillus paracasei* or progeny thereof or the aforementioned pharmaceutical composition is administered by a method selected from the group consisting of oral administration, injection administration (e.g., intravenous injection or intramuscular injection), or any combination thereof.

In certain embodiments, the subject is a mammal.

In certain embodiments, the subject is a human.

In a ninth aspect, the present invention provides a use of the aforementioned *Lactobacillus paracasei* or progeny thereof or the aforementioned composition or the aforementioned culture in the manufacture of a starter culture, in which the starter culture is useful in the fermentation of a solid food (e.g., cheese) or a liquid food (e.g., yogurt, flavored fermented milk, lactic acid bacteria beverage).

Beneficial Effect

The *Lactobacillus paracasei* of the present application has good tolerance to the acidic environment of gastric juice and bile salts, and has high capability to adhesion to the intestinal tract, and can activate the activity of macrophages and promote the expression of cytokines. In particular, the *Lactobacillus paracasei* of the present application can significantly increase the expression of anti-inflammatory factor IL-10, can inhibit inflammation or alleviate inflammatory diseases, and improve immunity. In addition, the *Lactobacillus paracasei* of the present application can reduce the level of serum IgE and improve allergic reactions.

The embodiments of the present invention will be described in detail below in conjunction with the accompanying drawings and examples. However, those skilled in the art will understand that the following drawings and examples are only used to illustrate the present invention, but not to limit the scope of the present invention. According to the accompanying drawings and the following detailed description of the preferred embodiments, various objects and advantageous aspects of the present invention will become apparent to those skilled in the art.

Figure 1:
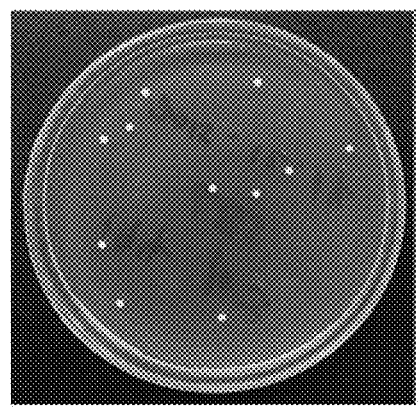
FIG. 1 shows the colony morphology of *Lactobacillus paracasei* 207-27 cultured on the plate.

Notes on the Deposition of Biological Materials

The *Lactobacillus paracasei* 207-27 has been deposited in the Guangdong Microbial Culture Collection Center (GDMCC) located on the 5th floor of Building 59, No. 100, Xianlie Middle Road, Guangzhou. It has the accession number GDMCC No. 60960, and the deposit time is Jan. 15, 2020.

Specific Models for Carrying Out the Invention

The invention will now be described with reference to the following examples which are intended to illustrate the invention rather than limiting the invention.

Unless otherwise specified, the experiments and methods described in the examples are basically performed according to conventional methods well known in the art and described in various references. For example, conventional techniques such as immunology, biochemistry, chemistry, molecular biology, microbiology, cell biology, genomics, and recombinant DNA used in the present invention can be found in: Sambrook, Fritsch and Maniatis, "MOLECULAR CLONING: A LABORATORY MANUAL", $2^{nd}$ edition (1989); "CURRENT PROTOCOLS IN MOLECULAR BIOLOGY", Edited by F. M. Ausubel et al., (1987); "METHODS IN ENZYMOLOGY" (series, Academic Publishing Company): "PCR 2: A PRACTICAL APPROACH", Edited by M. J. MacPherson, B. D. Hames, and G. R. Taylor (1995); and ANIMAL CELL CULTURE, Edited by R. I. Frescheni (1987).

In addition, if the specific conditions were not specified in the examples, it should be carried out in accordance with the conventional conditions or the conditions recommended by the manufacturer. The reagents or instruments used without indicating the manufacturer thereof were all conventional products that could be purchased commercially. Those skilled in the art know that the embodiments describe the present invention by way of illustration, and are not intended to limit the protection scope claimed by the present invention. All publications and other references mentioned herein are incorporated into this application by reference in their entirety.

Example 1. Isolation and Identification of Strains

In the present application, 265 strains were isolated from stool samples of normal term neonates born in West China Women's and Children's Hospital of Sichuan University, and one strain of *Lactobacillus paracasei* was screened from them, and was named *Lactobacillus* paracasei 207-27. Among them, the inclusion criteria for newborns were: living in five districts of Chengdu; gestational age of 37-42 weeks, birth weight between 2500-4000 g, and the babies had no congenital abnormalities or birth defects. The exclusion criteria were: mothers had used antibiotics within one month before delivery; parents had infectious diseases such as AIDS, tuberculosis, hepatitis B, and newborns were not suitable for collecting feces due to severe diseases such as neonatal pneumonia.

Fresh feces were collected from 1-4 month infants and placed in aseptic feces collection tubes. After sampling, it was temporarily stored at 4° C. and sent to the laboratory at low temperature by the sampling personnel for dilution and culture of the stool sample. If it could not be operated immediately, it was stored under anaerobic condition at 4° C. and cultured on the same day.

Figure 2:
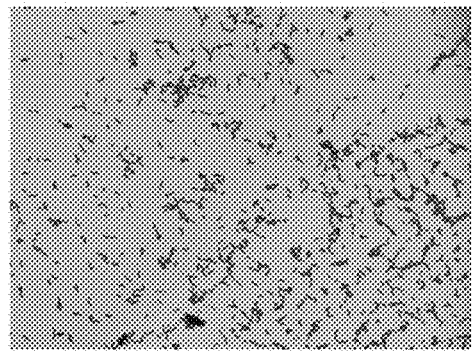
FIG. 2 shows a microscopic view of Gram-stained *Lactobacillus paracasei* 207-27.

0.5 g of feces was weighed, added with 4.5 mL of fecal diluent (4.5 g of $KH_2PO_4$, 6.0 g of $Na_2HPO_4$, 0.5 g of L-cysteine hydrochloride, 0.5 g of Tween-80, 1.0 g of agar were mixed with 1000 ml of distilled water, autoclaved for sterilization at 121° C. for 15 min for later use), shaken and mixed thoroughly, and diluted by 10 times in series. 100 µL of fecal mixture with suitable dilution degree was taken and spread on surface of *Lactobacillus* selective agar (84.0 g of LBS selective medium, 8.0 g of Lab-lemco powder (Oxoid), 15.0 g of sodium acetate·$3H_2O$, 1000 mL of pure water, 3.7 mL of acetic acid) by L-shaped rod, and anaerobic culture was carried out at 37° C. for 48 h. The suspected *Lactobacillus* colonies (usually white or slightly transparent, round with smooth edges) on the LBS plate were picked up, subcultured on MRS medium (Beijing Luqiao), and cultured under aerobic condition at 37° C. for 48 hours. Gram staining and microscopic observation were performed on the strains that could grow on MRS under aerobic condition, and the results were shown in FIG. 2. According to the oxygen demand of bacteria (facultative anaerobic type) and bacterial morphology (gram-positive, pleomorphic rods: long or slender rod-shaped, curved short rod, rod-shaped, clean-cut, generally arranged in chain, without spores), it was preliminarily judged to be *Lactobacillus*. Its cultivation shape on the plate was shown in FIG. 1.

After resuscitation and purification of the isolated strain, Wham's API 50 CH and 16S rDNA sequencing were used to identify the isolated *Lactobacillus* as *Lactobacillus paracasei*.

Furthermore, the whole genome of *Lactobacillus paracasei* 207-27 was determined using the PacBio Sequel2 sequencing platform, its genome length was 3,151,091 bp, the GC contents were 46.33% respectively (in which the GC contents referred to ratios of guanine and cytosine in the four bases of DNA), the chromosome genome contained 3,149 coding genes, 59 tRNA genes, 15 rRNA genes (including 5s rRNA, 16s rRNA and 23s rRNA), and 35 other types of RNA genes.

Based on the above-mentioned PCR identification and whole-genome sequencing experimental results, the present application obtained a new strain, i.e., *Lactobacillus paracasei* 207-27, which was deposited on Jan. 15, 2020.

Example 2. Study on the Probiotic Characteristics of *Lactobacillus Paracasei* 207-27

1. Experimental Screening for Acid and Bile Salt Tolerance of *Lactobacillus paracasei* 207-27

1.1 Preparation of test bacterial suspension: *Lactobacillus paracasei* 207-27 was resuscitated by MRS medium and subjected to passage twice for later use. After 48 hours of MRS culture, the bacteria were scraped into 2 mL of fecal diluent, vortexed and well mixed, and the concentration was roughly adjusted to $10^8$ to $10^9$ CFU/mL.

1.2 Preparation of Simulated Gastric Acid and Bile Salt Culture Solutions

Preparation of simulated gastric acid culture solution: MRS broth culture solution was prepared, sterilized and then adjusted with 1 mol/L HCL to pH value of 3.0, thereby preparing the simulated gastric acid culture solution.

Preparation of simulated bile salt culture solution: MRS broth culture solution was prepared, sterilized and then added with bovine bile salt to a concentration of 0.1%, adjust with 1 mol/L HCL to pH of 8.0, and then filtered for sterilization with 0.22 µm microporous membrane, thereby preparing the bile salt culture solution.

1.3 Gastric Acid and Bile Salt Tolerance Tests

Acid tolerance test of *Lactobacillus paracasei* 207-27: 0.9 ml of the simulated gastric acid culture solution was placed into a EP tube, added with 0.1 ml of the prepared bacterial suspension, vortexed and well mixed, and then it was placed in an anaerobic incubator and cultured at 37° C. for 2 hours. Tests were carried out at 0 h and 2 h, and 3 parallel tests were set for the strain at each time point. The MRS broth (pH=7) without adjusting the pH was used as control, the growth of bacteria was observed, and the death of bacteria caused by other factors was excluded.

Bile salt tolerance test of *Lactobacillus paracasei* 207-27: 0.9 ml of the bile salt culture solution was placed into a EP tube, added with 0.1 mL of the prepared bacterial suspension, vortexed and well mixed, and then it was placed in an anaerobic incubator and culture at 37° C. for 24 hours. Tests were carried out at 0 h and 24 h, and 3 parallel tests were set for the strain at each time point. The MRS broth (pH=7) without bile salt was used as control, the growth of bacteria was observed, and the death of bacteria caused by other factors was excluded.

After the above culture was completed, 10-fold gradient dilution was immediately carried out, the diluent with appropriate dilution degree was spot-inoculated to a MRS plate, cultured under anaerobic condition at 37° C. for 24-48 hours and subjected to counting. The counting result of the 0-hour dilution inoculation was used as the initial bacterial concentration. The results were compared with survival rates, which was calculated according to the following formula:

Survival rate(%)=concentration of viable bacteria after culture(CFU/mL)/0-hour concentration of viable bacteria(CFU/mL)×100

The experimental results showed that the survival rate of the *Lactobacillus paracasei* 207-27 after 2 hours of digestion in the simulated gastric acid culture solution of pH=3 was 81.3%; the survival rate after 24 hours of culture in the bile salt culture solution was 78.9%. Therefore, it could be seen that the *Lactobacillus paracasei* 207-27 had good tolerance to gastric acid and bile salts, and could effectively resist the extreme environment of the upper digestive tract, so as to reach the lower digestive tract, such as the colon, to perform healthy functions. The *Lactobacillus* paracasei 207-27 therefore meets the basic requirements as a probiotic.

2. Adhesion Ability of *Lactobacillus paracasei* 207-27 to Intestinal Mucosa 2.1 Adhesion test method: After resuscitating and subculturing *Lactobacillus paracasei* 207-27 on the MES plate for three generations, the OD600 absorbance of the bacterial suspension was adjusted to 0.597±0.005 (concentration of $1 \times 10^9$ CFU/mL). The commercial strains *Bifidobacterium animalis* subsp. *Lactis* BB-12 and *Lactobacillus rhamnosus* LGG were used as control strains for parallel experiments, and their bacterial suspensions were prepared according to the same method described above.

500 μg/mL mucin solution was added to 96-well Maxisorp plate (Nunc), 100 μL per well, and incubated overnight in a refrigerator at 4° C. It was taken out and washed with PBS three times, 200 μL per well, then blocked with PBS containing 1% Tween 20 for 1 h, 100 μL per well. 100 μL of the prepared bacterial suspension was taken and added to microwell, and 3 parallels were set for each strain. At the same time, PBS was used instead of bacterial suspension to be added as a blank control, and 3 parallels were set. Incubation was carried out overnight in a refrigerator at 4° C. After the incubation, it was taken out and washed three times with PBS containing 0.05% Tween 20 to remove unadhered bacteria. Then, it was dried in an oven at 60° C. for 1 h. The dried microplate was added with 1% crystal violet solution, 1004, per well, and stained for 45 min. Then it was washed with PBS for 6 times, added with absolute ethanol, and allowed to stand for 10 minutes to release the staining solution. Finally, the absorbance of each well at wavelength of 590 nm was measured by a microplate reader.

2.2 Adhesion results of *Lactobacillus paracasei* 207-27: The adhesion test results of *Lactobacillus paracasei* 207-27 were shown in Table 1.

TABLE 1

Adhesion test results

| No. | Strain No. | Stain | OD$_{590}$ value ($\overline{X} \pm S$) |
|---|---|---|---|
| 1 | 207-27 | L. paracasei | 0.613 ± 0.026 |
| 2 | LGG | L. rhamnosus | 0.609 ± 0.018 |
| 3 | Bb-12 | B. animalis | 0.696 ± 0.021 |
| 4 | Blank control | — | 0.089 ± 0.003 |

Mucin is the main component of intestinal epithelial cells that produce a large amount of mucus. Mucus can protect intestinal mucosal cells from contact with pathogenic microorganisms, prevent pathogenic bacteria from invading epithelial cells, thereby protecting the normal function of epithelial cells. Studies have shown that probiotics can induce intestinal epithelial cells to secrete mucin that forms a biofilm on the surface of the intestinal mucosa by occupying the attachment points of the intestinal mucosa, preventing foreign bacteria from attaching to the intestinal mucosa. The oligosaccharide chain of mucin contains a large number of specific sites that bind to various probiotics, especially the epitope at the end of the saccharide chain can also screen and identify the flora of intestinal probiotics, and assist the colonization of intestinal probiotics.

The results of this experiment showed that *Lactobacillus paracasei* 207-27 had similar mucin binding ability as compared with the commercial strains *Bifidobacterium animalis* BB12 and *Lactobacillus rhamnosus* LGG. Therefore, the applicant believes that *Lactobacillus paracasei* 207-27 can effectively adhere to the intestinal mucosa and has excellent colonization ability. Based on this, it occupies the surface of the intestinal mucosa, forms a probiotic barrier, inhibits the colonization and invasion of harmful bacteria, thereby effectively regulating the intestinal flora and protecting the normal immune function of the intestinal immune cells.

Example 3. Immune Properties of *Lactobacillus paracasei* 207-27 by Cell Experiment 1. Experimental Method Mouse macrophages RAW264.7 ($5 \times 10^5$/mL) were cultured, the *Lactobacillus paracasei* 207-27 suspension was adjusted to have concentration of $10^9$ CFU/mL, diluted by 10 times and co-cultured with cells, and used as the experimental group; PGN was used as a positive control (PGN was peptidoglycan of gram-positive bacteria, as the main substance that gram-positive bacteria stimulated and induced inflammation of host immune cells, so it was used as a positive control for this experiment), the commercial strain *Lactobacillus rhamnosus* LGG was used as standard strain control of *Lactobacillus*, RPMI1640 medium was used as blank control, three parallel samples were set up for each group. After 24 hours of co-cultivation, the cell supernatant was collected, and the secretion levels of the cytokine expression proteins as shown in Table 2 were detected by the enzyme-linked immunosorbent assay (ELISA) method.

2. Experimental Results and Analysis of Mouse Macrophages RAW264.7

2.1 Results and Analysis of Enzyme-Linked Immunosorbent Assay

The results of the ELISA experiment of co-culture of *Lactobacillus paracasei* 207-27 and mouse macrophages RAW264.7 were shown in Table 2.

TABLE 2

ELISA test results (mean ± standard deviation)

| | | Cytokine expression level (pg/mL) | | |
|---|---|---|---|---|
| Strain No. | Strain | IL-6 | IL-10 | TNF-α |
| 207-27 | L. paracasei | 86.44 ± 48.86 | 49 59 ± 4.44 | 5744.22 ± 236.56 |
| LGG | L. rhamnosus | 44.93 ± 39.48 | 92.07 ± 19.01 | 8097.62 ± 1006.08 |
| PGN | — | 926.95 ± 77.38 | 660.64 ± 87.83 | 9669.20 ± 16.37 |
| Control group | — | 16.23 ± 22.80 | 11.90 ± 2.80 | — |

The results showed that, compared with the control group, *Lactobacillus paracasei* 207-27 could stimulate the increase of the expression levels of the genes of cytokines IL-6, IL-10 and TNF-α, and induced the activation of macrophages.

Example 4. Immunomodulatory Ability Test of *Lactobacillus paracasei* 207-27

1. Experimental Method:

A total of 18 BALB/C mice, male, 6 weeks old, weighing 18-20 g, were selected. They were divided into 3 groups, including: 6 animals in the control group, 6 animals in the intervention control group of commercial probiotic strain LGG, which had been proved to have the most significant immunomodulatory ability in animal and clinical trials, and 6 animals in the intervention control group of *Lactobacillus paracasei* 207-27. The animals of the control group were given 0.2 ml of normal saline per day, and the animals of the probiotic intervention groups were given 0.2 ml of bacterial solution per day (the bacterial content was $10^9$ cfu). The animals of each group were raised for 4 weeks and then sacrificed.

Sample collection: On the day before the start of the gavage experiment, all mice were weighed and their feces were collected. On the $14^{th}$ day of the experiment, all mice were weighed and their feces were collected. On the $28^{th}$ day of the experiment, all mice were weighed and their feces were collected, then they were sacrificed, and their organs (spleen, lung, thymus, liver) were collected and weighed.

Measurement of indicators: the organ coefficients of spleen and thymus were determined by use weighing method; the expression of cytokine genes in spleen tissue was determined by RT-PCR method.

2. Experimental Results:

There was no significant difference in body weight in each group before and after the intervention, indicating that *Lactobacillus paracasei* 207-27 had no adverse effect on the normal development of mice. There was no significant difference in spleen coefficient and thymus coefficient between the groups, indicating that the exertion of probiotics' immunomodulatory effect would not affect the normal function of the organs. The animal experiments showed that *Lactobacillus paracasei* 207-27 activated macrophages and stimulated the secretion of various related cytokines, and the activation ability was higher than that of the commercial strain LGG (Table 3). In particular, IL-10 increased significantly. IL-10 was a multifunctional negative regulatory cytokine; the promoted secretion of a large amount of anti-inflammatory factor IL-10 when the probiotic activated pro-inflammatory responses (production of IL-6 and TNF-α) indicated that *Lactobacillus paracasei* 207-27 could balance the inflammatory responses and maintain the homeostasis of cellular immunity. The results of animal experiments were consistent with the results of cell experiments.

TABLE 3

Relative expression level of cytokine mRNA in spleen

| Group | IL-10 | IL-6 | IL-12 | TNF-a |
|---|---|---|---|---|
| Control group | 1.15 ± 0.28 | 1.19 ± 0.55 | 1.18 ± 0.62 | 0.99 ± 0.47 |
| LGG group | 0.47 ± 0.14 | 0.87 ± 0.3 | 0.35 ± 0.11 | 0.32 ± 0.11 |
| 207-27 group | 3.35 ± 1.36 | 1.63 ± 0.62 | 2.98 ± 1.39 | 2.78 ± 1.07 |

Example 5. Test of *Lactobacillus paracasei* 207-27 Inhibiting Allergic Reaction 1. Experimental Method:

In this experiment, ovalbumin (OVA) was used to establish a mouse serum IgE hypersensitivity model. The commercial probiotic strain LGG that had been shown to have a significant ability to inhibit allergic reactions in animal and clinical trials was used as a control to study the effect of *Lactobacillus paracasei* 207-27 on the inhibition of allergic reactions.

Experimental grouping: a total of 60 male BALB/C mice, 6 weeks old, 18-20 g, were selected, and grouped as shown in Table 4:

TABLE 4

Grouping of experimental animals

| Group | Number | Gavage and intervention |
|---|---|---|
| Control group | 15 | 0.2 ml normal saline gavage + normal saline injection |
| Model group | 15 | 0.2 ml normal saline gavage + OVA intervention |
| 207-27 test group | 15 | 0.2 ml 207-27 + OVA intervention |
| LGG+OVA group | 15 | 0.2 ml LGG + OVA intervention |

Intervention: The OVA reagent was 40 ug OVA+0.2 ml $AL(OH)_3$ adjuvant (absolute dose was 4 mg of $AL(OH)_3$). The absolute dose of the probiotic group was $10^9$ CFU, and the gavage volume was 0.2 ml/animal/day. After feeding for 42 days, 4 intraperitoneal OVA injection interventions were performed on the day 7, day 21, day 28, and day 35, respectively.

Sample collection and detection: The animals were sacrificed on the day 42, and the serum IgE contents and the expression of spleen cytokines were determined.

Figure 3:
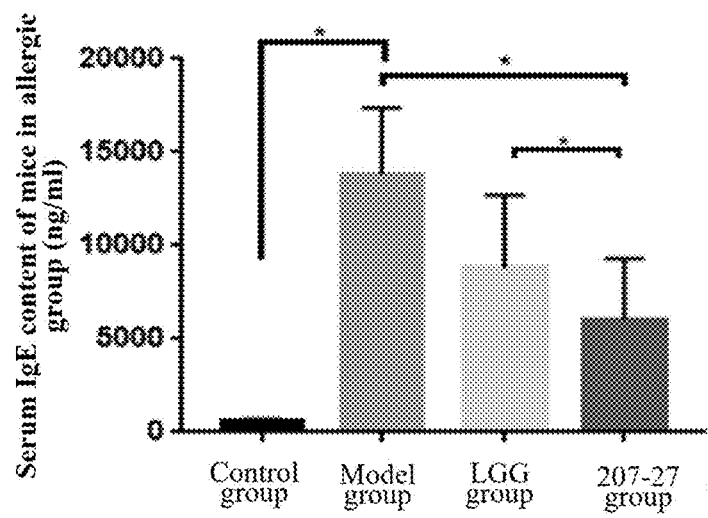
FIG. 3 shows the serum IgE levels of OVA model mice that received or did not receive treatment with *Lactobacillus paracasei* 207-27.

2. Experimental Results:

IgE is the main mediator of type I hypersensitivity, and the type I hypersensitivity is the main physiological mechanism of most allergic diseases. The results showed that *Lactobacillus* paracasei 207-27 could reduce the level of serum IgE in allergic mouse model, inhibit IgE-mediated allergic reactions, and alleviate allergic diseases (FIG. 3). This experiment also showed that the ability of *Lactobacillus paracasei* 207-27 to reduce serum IgE was higher than that of the commercial strain LGG.

The detection results of spleen cytokines showed that *Lactobacillus paracasei* 207-27 significantly increased the expression of anti-inflammatory factor IL-10 in spleen (Table 5). There are reports showing that IL-10 can participate in the regulation of TH1 and TH2. Based on the analysis of the above results, it is believed that the probiotics of the present application can induce the expression of IL-10, thereby inhibiting the activity of TH1 and TH2 cells, and down-regulating the body's immune response level, thereby achieving allergic reactions.

TABLE 5

Relative expression level of IL-10 cytokine mRNA in spleen

| Group | Relative expression level of mRNA IL-10 |
|---|---|
| Blank control group | 1.69 ± 0.95 |
| OVA model group | 1.03 ± 0.32 |
| 207-27 + OVA group | 5.79 ± 0.85 |
| LGG + OVA group | 1.84 ± 0.89 |

What is claimed is:

1. A food product comprising a *Lactobacillus paracasei* 207-27 and an additive,
    wherein the *Lactobacillus paracasei* is deposited in Guangdong Microbial Culture Collection Center, and has an accession number of GDMCC No. 60960; and
    wherein the additive is selected from the group consisting of dietary fiber, prebiotic, protein, lipid, plant polyphenol, or any combination thereof.

2. The food product according to claim 1, wherein the food product further comprises a microorganism selected from the group consisting of bacterium, fungus, or combination thereof.

3. The food product according to claim 2, characterized by one or more of the following:
(1) the microorganism is a probiotic;
(2) the bacterium is selected from the group consisting of *Lactobacillus* spp., *Bifidobacterium* spp., *Bacillus* spp., *Propionibacterium* spp., *Streptococcus* spp., *Lactococcus* spp., *Pediococcus* spp., *Enterococcus* spp., *Staphylococcus* spp., or any combination thereof;
(3) the fungus is a yeast; and
(4) the fungus is selected from the group consisting of *Saccharomyces cerevisiae*, *Saccharomyces boulardii*, *Kluyveromyces marxianus*, or any combination thereof.

4. The food product according to claim 3, characterized by one or more of the following:
(1) the bacterium of the *Lactobacillus* spp. is selected from the group consisting of: *Lactobacillus paracasei*, *Lactobacillus acidophilus*, *Lactobacillus brevis*, *Lactobacillus jensenii*, *Lactobacillus iners*, *Lactobacillus casei*, *Lactobacillus crispatus*, *Lactobacillus curvatus*, *Lactobacillus delbrueckii*, *Lactobacillus fermentum*, *Lactobacillus gasseri*, *Lactobacillus helveticus*, *Lactobacillus johnsonii*, *Lactobacillus plantarum*, *Lactobacillus reuteri*, *Lactobacillus rhamnosus*, *Lactobacillus sakei*, *Lactobacillus salivarius*, or any combination thereof;
(2) the bacterium of the *Bifidobacterium* spp. is selected from the group consisting of: *Bifidobacterium animalis*, *Bifidobacterium bifidum*, *Bifidobacterium breve*, *Bifidobacterium infantis*, *Bifidobacterium longum*, *Bifidobacterium adolescentis*, or any combination thereof;
(3) the bacterium of the *Bacillus* spp. is selected from the group consisting of: *Bacillus subtilis*, *Bacillus coagulans*, or any combination thereof;
(4) the bacterium of the *Propionibacterium* spp. is selected from the group consisting of: *Propionibacterium shermanii*, *Propionibacterium freudenreichii*, *Propionibacterium acidipropionici*, or any combination thereof;
(5) the bacterium of the *Streptococcus* spp. is selected from the group consisting of: *Streptococcus thermophilus*, *Streptococcus salivarius*, or any combination thereof;
(6) the bacterium of the *Lactococcus* spp. is *Lactococcus lactis*; and
(7) the bacterium of the *Enterococcus* spp. is selected from the group consisting of: *Enterococcus faecalis*, *Enterococcus faecium*, *Enterococcus mundtii*, or any combination thereof.

5. The food product according to claim 1, wherein:
(1) the food product further comprises a nutrient;
(2) the food product is used as a starter culture;
(3) the *Lactobacillus paracasei* in the food product is used as a starter culture to participate in a fermentation process; and/or
(4) the *Lactobacillus paracasei* is present in the food product in an amount of $10^6$ to $10^{12}$ CFU/dose.

6. The food product according to claim 5, characterized by one or more of the following:
(1) the starter culture is a starter culture for plant fermented product or a starter culture for dairy product; and
(2) the *Lactobacillus paracasei* is present in the food product in an amount of $10^8$ to $10^{12}$ CFU/dose.

7. The food product according to claim 1, characterized by one or more of the following:
(1) the food product is selected from the group consisting of a beverage, candy, fruit juice, or dairy product;
(2) the food product is selected from the group consisting of yogurt, flavored fermented milk, a beverage comprising lactic acid bacteria and cheese;
(3) the *Lactobacillus paracasei* is present in an amount of $10^6$ to $10^{12}$ CFU/dose in the food product or dietary supplement; and
(4) the *Lactobacillus paracasei* is present in an amount of $10^8$ to $10^{12}$ CFU/dose in the food product or dietary supplement.

8. A pharmaceutical composition, which comprises a *Lactobacillus paracasei* 207-27; and a pharmaceutically acceptable carrier:
wherein the *Lactobacillus paracasei* is deposited in Guangdong Microbial Culture Collection Center, and has an accession number of GDMCC No. 60960; and
wherein the pharmaceutical composition is in the form of a pill, powder, capsule, tablet, granule powder, opercula, orally dissolving granule, sachet, dragee or liquid.

9. The pharmaceutical composition according to claim 8, characterized by one or more of the following:
(1) the pharmaceutical composition comprises a formulation of the *Lactobacillus paracasei*;
(2) the pharmaceutical composition is formulated for oral administration;
(3) the *Lactobacillus paracasei* is present in an amount of $10^6$ to $10^{12}$ CFU/dose in the pharmaceutical composition; and
(4) the *Lactobacillus paracasei* is present in an amount of $10^8$ to $10^{12}$ CFU/dose in the pharmaceutical composition.

10. A method for manufacturing a starter culture, which comprises administering the *Lactobacillus paracasei* 207-27 according to claim 1 in the fermentation of a solid food or liquid food.

11. The method according to claim 10, characterized by one or two of the following:
(1) the solid food is cheese; and
(2) the liquid food is yogurt, flavored fermented milk, lactic acid bacteria drinks, or any combination thereof.

* * * * *